US008335655B2

(12) United States Patent
Olson et al.

(10) Patent No.: US 8,335,655 B2

(45) Date of Patent: Dec. 18, 2012

(54) INTELLIGENT SATURATION CONTROL FOR COMPOUND SPECIFIC OPTIMIZATION OF MRM

(75) Inventors: Loren Y. Olson, San Jose, CA (US); Anthony J. Romanelli, Milford, MA (US); John Joseph Gibbons, Brampton (CA); April L. Thomas, Marshfield, MA (US); Elliott B. Jones, San Francisco, CA (US); Hua-fen Liu, San Jose, CA (US)

(73) Assignee: DH Technologies Development Pte. Ltd., Singapore (SG)

( * ) Notice: Subject to any disclaimer, the term of this patent is extended or adjusted under 35 U.S.C. 154(b) by 452 days.

(21) Appl. No.: 12/476,133

(22) Filed: Jun. 1, 2009

(65) Prior Publication Data

US 2009/0299671 A1 Dec. 3, 2009

Related U.S. Application Data

(60) Provisional application No. 61/057,733, filed on May 30, 2008.

(51) Int. Cl.
*G01N 33/50* (2006.01)
*G01N 33/48* (2006.01)

(52) U.S. Cl. .......................................................... 702/19

(58) Field of Classification Search ......................... None
See application file for complete search history.

(56) References Cited

OTHER PUBLICATIONS

Kerns et al. (Integrated high capacity solid phase extraction-MS/MS system for pharmaceutical profiling in drug discovery, Journal of Pharmaceutical and Biomedical Analysis, 2004, vol. 34, pp. 1-9.*

* cited by examiner

*Primary Examiner* — Jason Sims

(74) *Attorney, Agent, or Firm* — John R. Kasha; Kasha Law LLC

(57) ABSTRACT

Mass spectrometer parameters used to tune a mass spectrometer for multiple reaction monitoring (MRM) are determined from a single injection of a sample. Two or more precursor ion scans and a plurality of product ion scans for each precursor ion scan are performed from the injection. Each precursor ion scan is produced with different mass spectrometer parameters that create a different level of ion current. The mass spectra of the precursor ion scans are analyzed to determine if saturation has occurred in any of the precursor ion scans. A precursor ion scan that produces the highest ion current with the least amount of saturation is selected. The mass spectrometer parameters used to tune the mass spectrometer for MRM are determined from (1) the mass spectrometer parameters of the selected precursor ion scan and (2) the mass spectrometer parameters of product ion scans from fragments of the selected precursor ion scan.

20 Claims, 4 Drawing Sheets

INTELLIGENT SATURATION CONTROL FOR COMPOUND SPECIFIC OPTIMIZATION OF MRM

CROSS-REFERENCE TO RELATED APPLICATION

This application claims the benefit of U.S. Provisional Patent Application No. 61/057,733 filed May 30, 2008 (the "'733 application"), which is incorporated by reference herein in its entirety.

INTRODUCTION

Modem drug discovery environments often rely heavily on the quality and accuracy of early in vitro and in vivo studies to select programs with a high potential for success. The high research and development cost and fast pace at which modem medicinal chemists can synthesize new compounds places a high demand for throughput and quality on absorption, distribution, metabolism, and excretion (ADME) groups and pharmacokinetics (PK) groups. In the laboratories of these groups, it is common for hundreds of new chemical entities to be screened through essays each week. Handling a large number of diverse analytes presents a significant logistical problem. These diverse analytes can include compound libraries, dilutions of powders, stocks for liquid chromatography mass spectrometry mass spectrometry (LC/MS/MS) optimization, assay samples, and standards. Handling these diverse analytes in drug discovery environments often results in workflow bottlenecks.

BRIEF DESCRIPTION OF THE DRAWINGS

The skilled artisan will understand that the drawings, described below, are for illustration purposes only. The drawings are not intended to limit the scope of the present teachings in any way.

Figure 1:
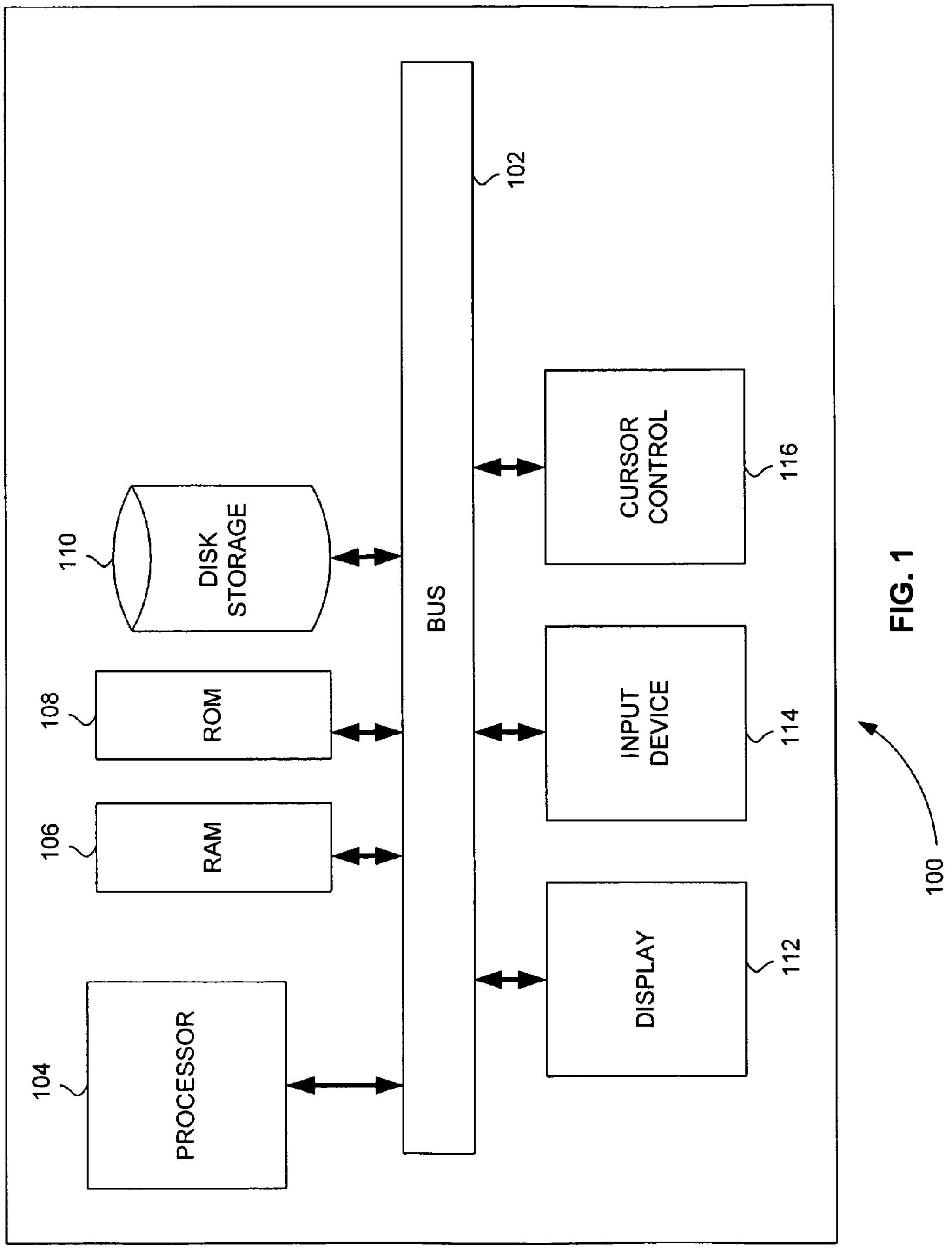
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. The present teachings are capable of other embodiments and of being practiced or being carried out in various ways. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for determining base calls, and instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Definitions

For the purposes of interpreting this specification, the following definitions will apply and whenever appropriate, terms used in the singular will also include the plural and vice versa. The definitions set forth below shall supercede any conflicting definitions in any documents incorporated herein by reference.

As used herein, "compound" or "analyte" refers to a molecule of interest that may be determined. Non-limiting examples of analytes can include, but are not limited to, proteins, peptides, nucleic acids (both DNA or RNA), carbohydrates, lipids, steroids and/or other small molecules with a molecular weight of less than 1500 Daltons. The source of the analyte, or the sample comprising the analyte, is not a limitation as it can come from any source. The analyte or analytes can be natural or synthetic.

Non-limiting examples of sources for the analyte, or the sample comprising the analyte, include, but are not limited to, cells or tissues, or cultures (or subcultures) thereof. Non-limiting examples of analyte sources include, but are not limited to, crude or processed cell lysates (including whole cell lysates), body fluids, tissue extracts or cell extracts. Still other non-limiting examples of sources for the analyte include, but are not limited to, fractions from a separation technique such as a chromatographic separation or an electrophoretic separation.

Body fluids include, but are not limited to, blood, urine, feces, spinal fluid, cerebral fluid, amniotic fluid, lymph fluid or a fluid from a glandular secretion. By processed cell lysate it is meant that the cell lysate is treated, in addition to the treatments needed to lyse the cell, to thereby perform additional processing of the collected material. For example, the sample can be a cell lysate comprising one or more analytes that are peptides formed by treatment of the total protein component of a crude cell lysate with a proteolytic enzyme to thereby digest precursor protein or proteins.

As used herein, declustering potential (DP) is synonymous with cone voltage or interface voltage. Also, the terms "voltage" and "potential" are interchangeable.

In various embodiments the processing of a sample or sample mixture of analytes can involve separation. The separation can be performed by chromatography. For example, liquid chromatography/mass spectrometry (LC/MS) or chromatography/mass spectrometry/mass spectrometry (LC/MS/MS) can be used to effect such a sample separation and mass analysis. Moreover, any chromatographic separation process suitable to separate the analytes of interest can be used. For example, the chromatographic separation can be normal phase chromatography, reversed-phase chromatography, ion-exchange chromatography, size exclusion chromatography, or affinity chromatography.

The separation can be performed electrophoretically. Non-limiting examples of electrophoretic separations techniques that can be used include, but are not limited to, one-dimensional electrophoretic separation, two-dimensional electrophoretic separation, and/or capillary electrophoretic separation.

As used herein, "fragmentation" refers to the breaking of a covalent bond. As used herein, "fragment" refers to a product of fragmentation (noun) or the operation of causing fragmentation (verb).

The methods and systems in various embodiments can be practiced using tandem mass spectrometers and other mass spectrometers that have the ability to select and fragment molecular ions. A tandem mass spectrometer performs a first mass analysis followed by a second mass analysis or mass spectrometry/mass spectrometry (MS/MS). Tandem mass spectrometers have the ability to select molecular ions (precursor ions) according to their mass-to-charge (m/z) ratio in a first mass analyzer, and then fragment the precursor ion and record the resulting fragment (daughter or product) ion spectra using a second mass analyzer. A mass analyzer is a single-stage mass spectrometer, for example. More specifically, product fragment ion spectra can be generated by subjecting precursor ions to dissociative energy levels (e.g. collision-induced dissociation (CID)) using a second mass analyzer. For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, linear ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and high-energy CID using MALDI-TOF (time of flight)-TOF MS.

Methods of Data Processing

In most high throughput multiple reaction monitoring (MRM) workflows users tend to make one concentration for all analytes for tuning purposes. If a signal is too low the stock needs to be remade. Thus the users tend to use concentrations that are higher so most of the analytes can be tuned successfully. However if the signal is too high, the quality of the tune begins to be compromised. In various embodiments, the tuning process can compensate for this problem and adjust the signal so it is in the optimal range. This makes the user's workflow much easier as they do not need to dilute each analyte individually.

If the signal is too high, the detector of the mass spectrometer is overwhelmed and the signal is said to be saturated. Conventionally, if saturation is detected from a first injection of the analyte, a user creates a lower concentration of the analyte, performs a second injection of the lower concentration, and conducts the tuning experiment. Typically the first and second injections are manual injections.

In various embodiments, saturation analysis and correction is incorporated into the tuning experiments for MRM in an automated fashion. For example, a first injection of an analyte is performed by an automated injection device. An automated injection device can include, but is not limited to, a syringe of an autosampler. The automated injection device is connected to and controlled by a processor that performs a tuning algorithm using one or more software modules.

Upon receiving the first injection from the automated injection device, a mass spectrometer performs a precursor ion scan followed by a number of product ion scans for each of a number of fragments produced from the precursor ion scan according to the tuning algorithm. The mass spectrometer is also connected to and controlled by a processor. The mass spectrometer can be, but is not limited to, a triple quadrupole or a triple quadrupole linear ion trap hybrid instrument. The precursor ion scan is performed with a certain set of mass spectrometer parameters. The product ion scans for each fragment are performed with most of the same mass spectrometer parameters held constant while the collision energy (CE) is varied.

The tuning algorithm analyzes the mass spectrum produced by the precursor ion scan for saturation. If no saturation is found in the mass spectrum, the mass spectrometer parameters of the precursor ion scan and the mass spectrometer parameters of the best product ion scans for each fragment are used to develop an MRM table. Once the MRM table is complete, the mass spectrometer is tuned for the particular analyte. The MRM table is then used for all subsequent MRM runs of the analyte.

If saturation is detected in the mass spectrum produced by the precursor ion scan, the tuning algorithm attempts to correct for the saturation. In various embodiments, the tuning algorithm performs saturation correction by selecting mass spectrometer parameters based on non-saturated areas of the mass spectrum of the precursor ion scan.

In various embodiments, the tuning algorithm performs saturation correction by instructing the automated injection device to select a lower concentration of the analyte and perform a second injection. The precursor ion scan and the product ion scans are then repeated with the same mass spectrometer parameters.

In various embodiments, the tuning algorithm performs saturation correction by instructing the automated injection device to select the same concentration of the analyte and perform a second injection. The precursor ion scan and the product ion scans are then repeated with the different mass spectrometer parameters. The different mass spectrometer parameters are selected to attenuate the ion current so that saturation is limited at the detector. The mass spectrometer parameters that are selected to attenuate the ion current can include, but are not limited to, ion source conditions, interface voltages, axial ion path voltages, isolation mass, and quadrupole resolution. Ion source conditions can include, but are not limited to, the ion source voltage (ISV). Interface voltages can include, but are not limited to, the declustering potential (DP). Axial ion path voltages can include, but are not limited to, lens voltages or the collision energy (CE). Isolation mass can include, but is not limited to, the second or third most intense isotopes or product ions. In various embodiments, the tuning algorithm performs saturation correction by performing additional precursor and product ion scans using different mass spectrometer parameters from the first injection. As above, the different mass spectrometer parameters are selected to attenuate the ion current so that saturation is limited at the detector in each additional precursor ion scan. The improved scanning speeds of recent mass spectrometers allow two or more precursor ion scans followed by product ions scans to be performed on a single injection of an analyte within a reasonable time period. A first precursor ion scan followed by product ions scans can be performed before the saturation analysis and subsequent precursor ion scans followed by product ions scans can be made after the saturation analysis, for example. In various embodiments, the two or more precursor ion scans followed by product ions scans can be performed before saturation analysis and a precursor ion scan with the highest ion current and lowest saturation can be selected from the two or more precursor ion scans after saturation analysis.

Figure 2:
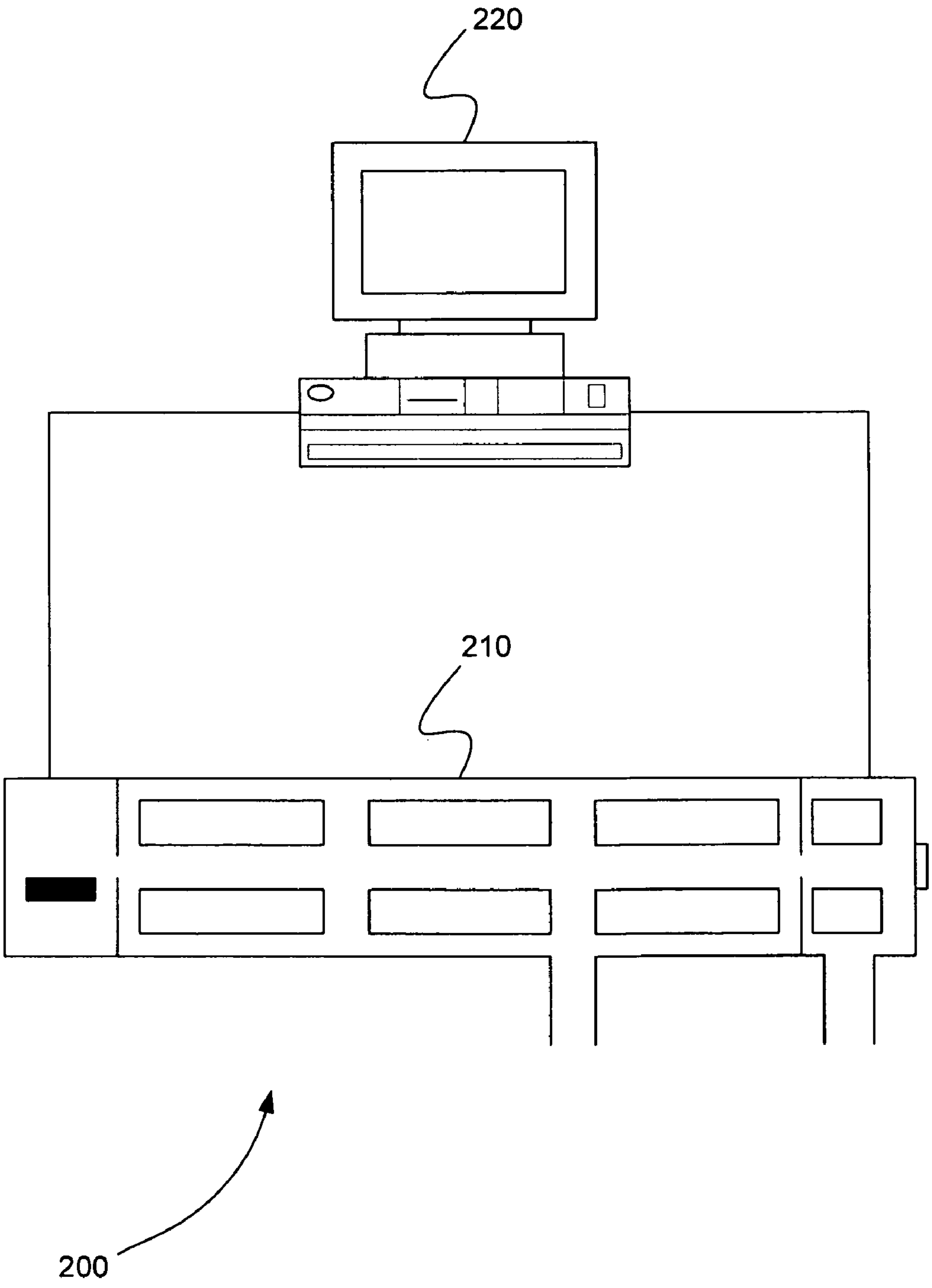
FIG. 2 is a schematic diagram showing a system for automatically determining mass spectrometer parameters used to tune a mass spectrometer for multiple reaction monitoring (MRM), in accordance with the present teachings.

FIG. 2 is a schematic diagram showing a system 200 for automatically determining mass spectrometer parameters used to tune a mass spectrometer for MRM, in accordance with the present teachings. System 200 includes mass spectrometer 210 and processor 220. As described above, mass spectrometer 210 can be, but is not limited to, a triple quadrupole or a triple quadrupole linear ion trap hybrid instrument a tandem mass spectrometer. Processor 220 can be, but is not limited to, a computer, microprocessor, or any device capable of sending and receiving control signals and data from mass spectrometer 210 and processing data.

Mass spectrometer 210 receives a single injection of a sample that includes an analyte. Mass spectrometer 210 performs two or more precursor ion scans and a plurality of product ion scans for each precursor ion scan of the two or more precursor ion scans from the single injection. Each precursor ion scan is produced with different mass spectrometer parameters that create a different level of ion current for the same precursor ion.

Processor 220 is in communication with the mass spectrometer 210. Processor 220 analyzes the mass spectra of the two or more precursor ion scans to determine if saturation has occurred in any of the two or more precursor ion scans. Processor 220 selects the precursor ion scan from the two or more precursor ion scans that produces the highest ion current with the least amount of saturation. Finally, processor 220 determines the mass spectrometer parameters used to tune the mass spectrometer for MRM from (1) the mass spectrometer parameters of the selected precursor ion scan and (2) the mass spectrometer parameters of the product ion scans from one or more fragments produced from the selected precursor ion scan.

Figure 3:
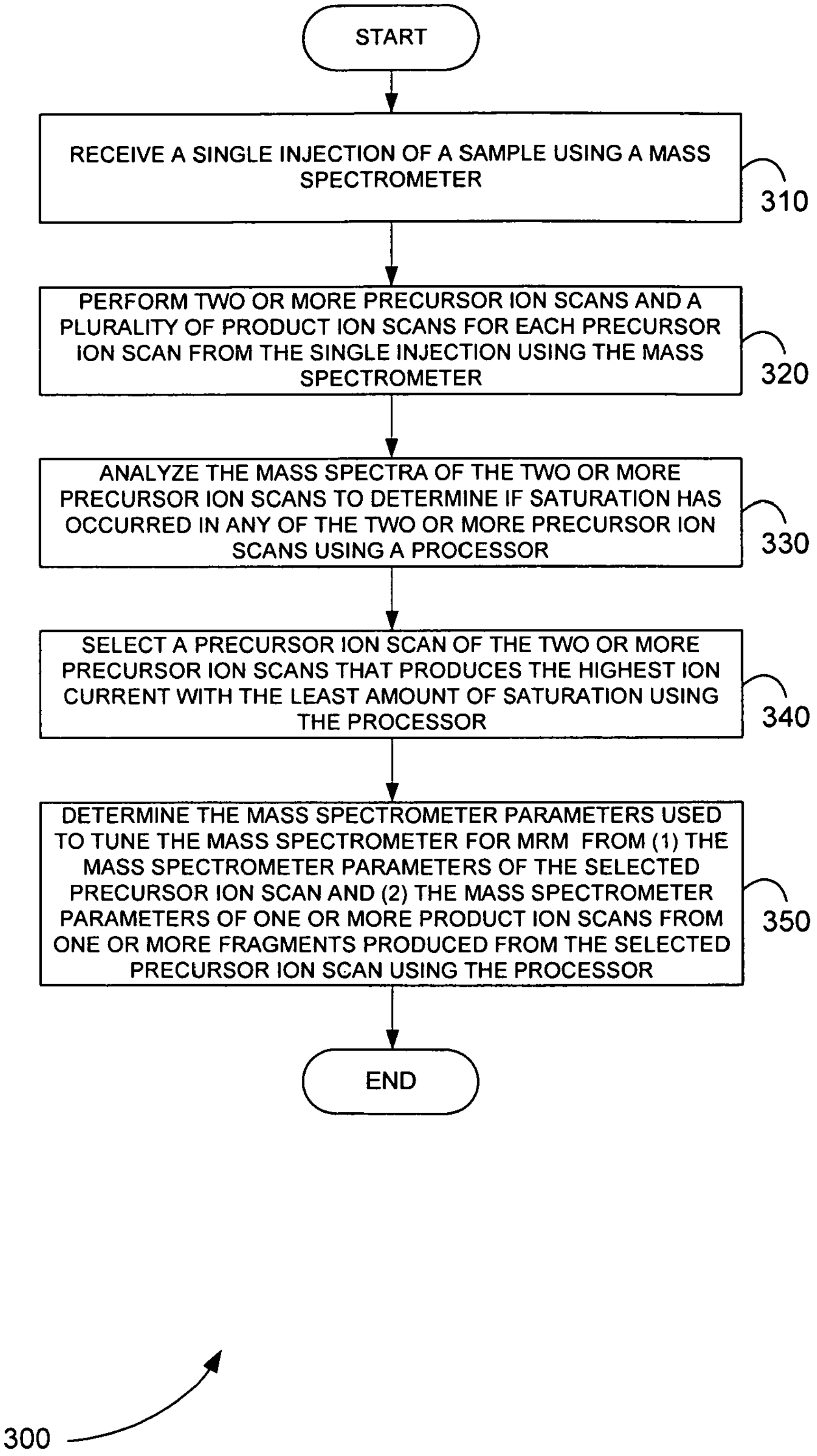
FIG. 3 is a flowchart showing a method for automatically determining mass spectrometer parameters used to tune a mass spectrometer for MRM, in accordance with the present teachings.

FIG. 3 is a flowchart showing a method 300 for automatically determining mass spectrometer parameters used to tune a mass spectrometer for MRM, in accordance with the present teachings.

In step 310 of method 300, a single injection of a sample is received using a mass spectrometer.

In step 320, two or more precursor ion scans and a plurality of product ion scans for each precursor ion scan of the two or more precursor ion scans are performed from the single injection using the mass spectrometer. Each precursor ion scan is produced with different mass spectrometer parameters that create a different level of ion current for the same precursor ion of the sample.

In step 330, the mass spectra of the two or more precursor ion scans are analyzed to determine if saturation has occurred in any of the two or more precursor ion scans using a processor.

In step 340, a precursor ion scan of the two or more precursor ion scans that produces the highest ion current with the least amount of saturation is selected using the processor.

In step 350, the mass spectrometer parameters used to tune the mass spectrometer for MRM are determined from (1) the mass spectrometer parameters of the selected precursor ion scan and (2) the mass spectrometer parameters of one or more product ion scans from one or more fragments produced from the selected precursor ion scan using the processor.

In various embodiments, a computer program product includes a tangible computer-readable storage medium whose contents include a program with instructions being executed on a processor so as to perform a method for automatically determining mass spectrometer parameters used to tune a mass spectrometer for MRM. This method is performed by a system of distinct software modules.

Figure 4:
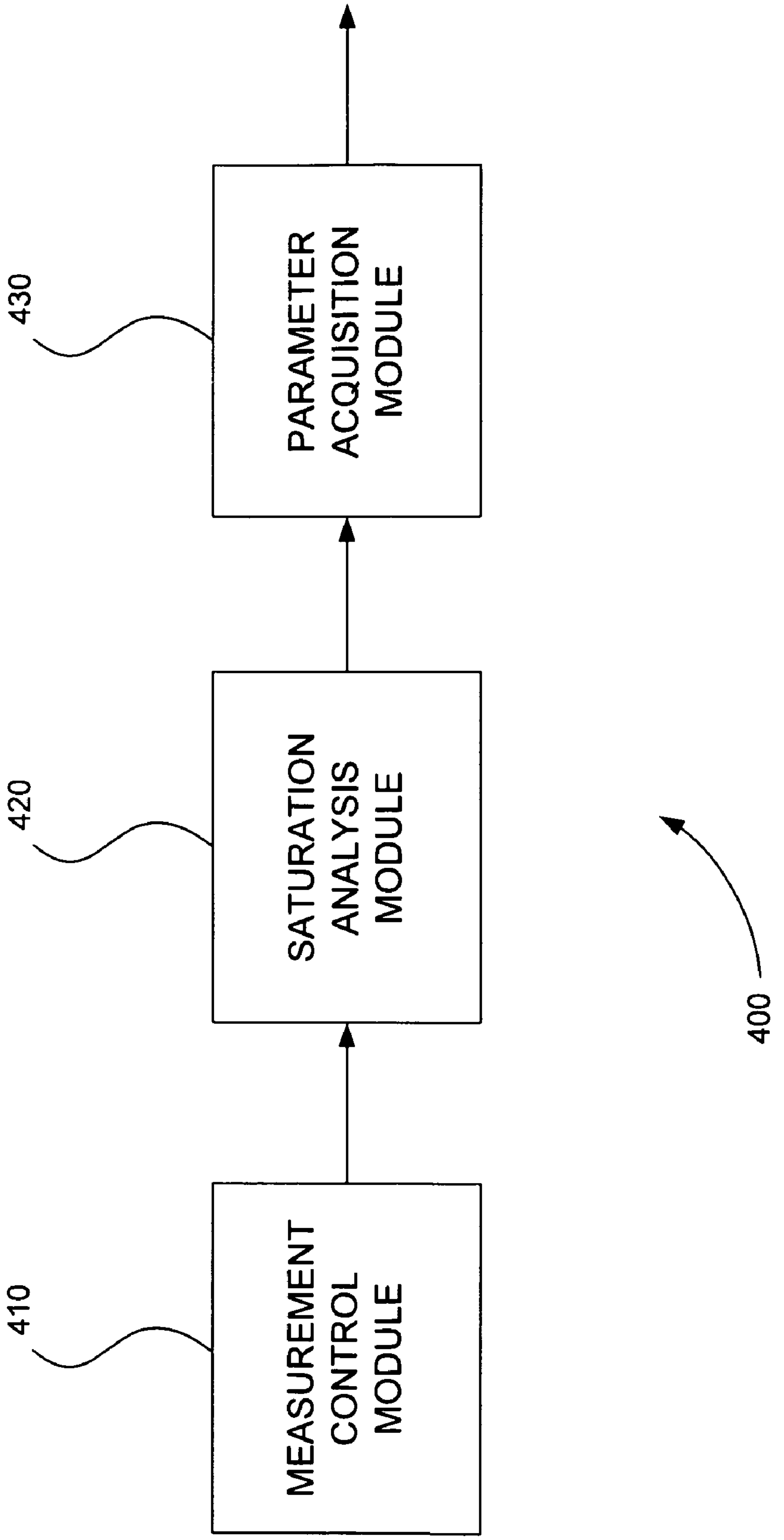
FIG. 4 is a schematic diagram of a system of distinct software modules that performs a method for automatically determining mass spectrometer parameters used to tune a mass spectrometer for MRM, in accordance with the present teachings.

FIG. 4 is a schematic diagram of a system 400 of distinct software modules that performs a method for automatically determining mass spectrometer parameters used to tune a mass spectrometer for MRM, in accordance with the present teachings. System 400 includes measurement control module 410, saturation analysis module 420, and parameter acquisition module 430.

A mass spectrometer is instructed to receive a single injection of a sample using measurement control module 410. The mass spectrometer is then instructed to perform two or more precursor ion scans and a plurality of product ion scans for each precursor ion scan of the two or more precursor ion scans from the single injection using measurement control module 410. Each precursor ion scan is produced with different mass spectrometer parameters that create a different level of ion current for the same precursor ion from the sample.

The mass spectra of the two or more precursor ion scans are analyzed to determine if saturation has occurred in any of the two or more precursor ion scans using saturation analysis module 420. A precursor ion scan of the two or more precursor ion scans that produces the highest ion current with the least amount of saturation is selected using saturation analysis module 420.

The mass spectrometer parameters used to tune the mass spectrometer for MRM are determined from (1) the mass spectrometer parameters of the selected precursor ion scan and (2) the mass spectrometer parameters of one or more product ion scans from one or more fragments produced from the selected precursor ion scan using parameter acquisition module 430.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for automatically determining mass spectrometer parameters used to tune a mass spectrometer for multiple reaction monitoring, comprising:

a mass spectrometer that receives a single injection of a sample and performs two or more precursor ion scans and a plurality of product ion scans for each precursor ion scan of the two or more precursor ion scans from the single injection, wherein the each precursor ion scan is produced with different mass spectrometer parameters that create a different level of ion current for a same precursor ion, a processor that is in communication with the mass spectrometer, wherein the processor analyzes mass spectra of the two or more precursor ion scans to determine if saturation has occurred in any of the two or more precursor ion scans and performs saturation correction for a precursor ion scan of the two or more precursor ion scans if saturation has occurred in the precursor ion scan, the processor selects a precursor ion scan of the two or more precursor ion scans that produces the highest ion current with the least amount of saturation, and the processor determines mass spectrometer parameters used to tune the mass spectrometer for multiple reaction monitoring from mass spectrometer parameters of the selected precursor ion scan and mass spectrometer parameters of one or more product ion scans from one or more fragments produced from the selected precursor ion scan.

2. The system of claim 1, wherein the spectrometer comprises a triple quadrupole.

3. The system of claim 1, wherein the spectrometer comprises a triple quadrupole linear ion trap hybrid instrument.

4. The system of claim 1, wherein the different mass spectrometer parameters that produce a different level of ion current for a sample precursor ion comprise an ion source condition.

5. The system of claim 1, wherein the different mass spectrometer parameters that produce a different level of ion current for a same precursor ion comprise an interface voltage.

6. The system of claim 1, wherein the different mass spectrometer parameters that produce a different level of ion current for a same precursor ion comprise an axial path ion voltage.

7. The system of claim 1, wherein the different mass spectrometer parameters that produce a different level of ion current for a same precursor ion comprise an isolation mass.

8. The system of claim 1, wherein the different mass spectrometer parameters that produce a different level of ion current for a same precursor ion comprise a quadrupole resolution.

9. A method for automatically determining mass spectrometer parameters used to tune a mass spectrometer for multiple reaction monitoring, comprising:

receiving a single injection of a sample using a mass spectrometer;

performing one or more precursor ion scans and a plurality of product ion scans for each precursor ion scan of the two or more precursor ion scans from the single injection using the mass spectrometer, wherein the each precursor ion scan is produced with different mass spectrometer parameters that create a different level of ion current for a same precursor ion;

analyzing mass spectra of the two or more precursor ion scans to determine if saturation has occurred in any of the two or more precursor ion scans and performing saturation correction for a precursor ion scan of the two or more precursor ion scans if saturation has occurred in the precursor ion scan using a processor;

selecting a precursor ion scan of the two or more precursor ion scans that produces the highest ion current with the least amount of saturation using the processor; and determining mass spectrometer parameters used to tune the mass spectrometer for multiple reaction monitoring from mass spectrometer parameters of the selected precursor ion scan and mass spectrometer parameters of one or more product ion scans from one or more fragments produced from the selected precursor ion scan using the processor.

10. The method of claim 9, wherein the different mass spectrometer parameters that produce a different level of ion current for a sample precursor ion comprise an ion source condition.

11. The method of claim 9, wherein the different mass spectrometer parameters that produce a different level of ion current for a same precursor ion comprise an interface voltage.

12. The method of claim 9, wherein the different mass spectrometer parameters that produce a different level of ion current for a same precursor ion comprise an axial path ion voltage.

13. The method of claim 9, wherein the different mass spectrometer parameters that produce a different level of ion current for a same precursor ion comprise an isolation mass.

14. The method of claim 9, wherein the different mass spectrometer parameters that produce a different level of ion current for a same precursor ion comprise a quadrupole resolution.

15. A computer program product, comprising a tangible computer-readable storage medium whose contents include a program with instructions being executed on a processor so as to perform a method for automatically determining mass spectrometer parameters used to tune a mass spectrometer for multiple reaction monitoring, the method comprising:

providing a system, wherein the system comprises distinct software modules, and wherein the distinct software modules comprise a measurement control module, a saturation analysis module, and a parameter acquisition module;

instructing a mass spectrometer to receive a single injection of a sample using the measurement control module;

instructing the mass spectrometer to perform one or more precursor ion scans and a plurality of product ion scans for each precursor ion scan of the two or more precursor ion scans from the single injection using the measurement control module, wherein the each precursor ion scan is produced with different mass spectrometer parameters that create a different level of ion current for a same precursor ion;

analyzing mass spectra of the two or more precursor ion scans to determine if saturation has occurred in any of the two or more precursor ion scans and performing saturation correction for a precursor ion scan of the two or more precursor ion scans if saturation has occurred in the precursor ion scan using the saturation analysis module;

selecting a precursor ion scan of the two or more precursor ion scans that produces the highest ion current with the least amount of saturation using the saturation analysis module; and determining mass spectrometer parameters used to tune the mass spectrometer for multiple reaction monitoring from mass spectrometer parameters of the selected precursor ion scan and mass spectrometer parameters of one or more product ion scans from one or more fragments produced from the selected precursor ion scan using the parameter acquisition module module.

16. The computer program product of claim 15, wherein the different mass spectrometer parameters that produce a different level of ion current for a sample precursor ion comprise an ion source condition.

17. The computer program product of claim 15, wherein the different mass spectrometer parameters that produce a different level of ion current for a same precursor ion comprise an interface voltage.

18. The computer program product of claim 15, wherein the different mass spectrometer parameters that produce a different level of ion current for a same precursor ion comprise an axial path ion voltage.

19. The computer program product of claim 15, wherein the different mass spectrometer parameters that produce a different level of ion current for a same precursor ion comprise an isolation mass.

20. The computer program product of claim 15, wherein the different mass spectrometer parameters that produce a different level of ion current for a same precursor ion comprise a quadrupole resolution.

* * * * *